(12) United States Patent
Seayad et al.

(10) Patent No.: US 6,444,844 B1
(45) Date of Patent: Sep. 3, 2002

(54) PROCESS FOR THE PREPARATION OF A CARBOXYLIC ACID

(75) Inventors: Abdul Majeed Seayad; Jayasree Seayad; Raghunath Vitthal Chaudhari, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/817,810

(22) Filed: Mar. 20, 2001

(51) Int. Cl.$^7$ .............................................. C07C 51/10
(52) U.S. Cl. ...................................................... 562/406
(58) Field of Search ................................ 562/406, 490, 562/521, 522, 517–519, 520

(56) References Cited

U.S. PATENT DOCUMENTS

| | | | |
|---|---|---|---|
| 4,990,658 A | * 2/1991 | Stahly et al. | ................ 562/406 |
| 5,315,026 A | * 5/1994 | Wu | ............................. 560/105 |
| 6,069,253 A | * 5/2000 | Chaudhari et al. | ............. 546/2 |

OTHER PUBLICATIONS

M. Dolors Miquel–Serrano et al, "Recoverable chiral palladium–sulfonated diphosphine catalysts for the asymmetric hydrocarboxylation of vinyl arenes", Tet. Asym., vol. 10 (1999), pp. 4463–4467.*

* cited by examiner

Primary Examiner—Paul J. Killos
(74) Attorney, Agent, or Firm—Ladas & Parry

(57) ABSTRACT

The present invention relates to a process for the preparation of a carboxylic acid of the formula III,

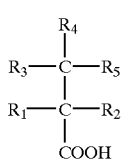

Formula III wherein $R_1$ is aryl, substituted aryl, naphthyl, substituted naphthyl or alkyl, $R_2$, $R_3$, $R_4$ and $R_5$ are independently hydrogen or alkyl, by reacting the corresponding olefin of formula I or the corresponding organic halide or alcohol of the formula II,

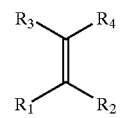

Formula I

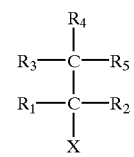

Formula II wherein $R_1$ is selected from the group consisting of aryl, substituted aryl, naphthyl, substituted naphthyl or alkyl, $R_2$, $R_3$, $R_4$ and $R_5$ are independently hydrogen or alkyl and X is a halogen atom or a —OH group, using a novel water soluble palladium complex catalyst of general formula IV

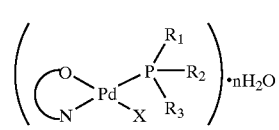

Formula IV wherein $R_1$, $R_2$ and $R_3$ are substituents on the phosphine ligand and selected from the group consisting of alkyl, aryl, arylalkyl, and cycloaliphatic, at least one of which carries a sulfonic acid and salts thereof, X is aryl or alkyl sulfonato or aryl or alkyl carboxylate or formato or a halide,

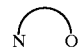

is an anionic chelating ligand containing a N donor and O— group.

20 Claims, No Drawings

PROCESS FOR THE PREPARATION OF A CARBOXYLIC ACID

FIELD OF THE INVENTION

This invention relates to an improved process for the preparation of a carboxylic acid. Particularly, this invention relates to an improved process for conversion of an olefin, organic halide or aryl alcohol to the corresponding saturated carboxylic acid.

BACKGROUND OF THE INVENTION

Aryl and aliphatic carboxylic acids have a variety of applications in industries as anti-inflammatory drugs, fine chemicals, etc. The prior art describes catalyst systems for employment in processes for the preparation of carboxylic acids by the carbonylation of corresponding alcohols, olefins or halo derivatives. The best known of such catalysts are homogeneous palladium catalysts. In the processes described in literature, the catalysts used were mainly $Pd(PPh_3)_2Cl_2$ or $PdCl_2$ or $Pd(OAc)_2$ along with excess phosphine ligands (EP 0,400,892A3, EP 0,284,310A1, U.S. Pat, No. 5,315,026, J. Mol. Catal., 1992, 77, 7–13, U.S. Pat. No. 5,260,477), which gave lower reactions rates (TOF= 25–35 $h^{-1}$) under mild conditions (130° C., 1000 psig). In the publications, Catalysis Letters 1999, 61, 1–2: 99–103 and Organic Letters, 1999, 1:1, 459–461, high reaction rates (TOF=up to 2600 $h^{-1}$) and 2-arylpropionic acid selectivity (>95%) was reported for the carbonylation of 1-arylethanols and vinyl aromatics using a catalyst system consisting of $PdCl_2(PPh_3)_2$/TsOH/LiCl in a homogeneous medium under relatively mild reaction conditions (115° C. and 800 psig). The U.S. Pat. No. 6093847 describes the carbonylation of 1-(4-isobutylphenyl)ethanol (IBPE) using novel Pd complexes having general formula V wherein $R'_1$, $R'_2$ and $R'_3$ are substituents on the phosphine ligand such as, alkyl, aryl, arylalkyl, cycloaliphatic, X is groups such as aryl or alkyl sulfonato or aryl or alkyl carboxylate or formato or halides such as $Cl^-$, $Br^-$, $I^-$,

is an anionic chelating ligand containing a N donor and O— group such as 8-hydroxyquinoline, 2-hydroxypyridine, (2-hydroxyethyl)pyridine, pyridil-2-, pyrezyl-2, piperidyl-2-, piperzyl-2-, quinolyl-2-, isoquinolyl-1- and isoquinolyl-2- carboxylates, particularly pyridyl-2-carboxylate, piperidyl-2-carboxylate and 8-hydroxyquinoline, which also gave high reaction rates and Ibuprofen selectivity under similar conditions.

A major disadvantage of all these processes is the difficulty in separation of the catalyst from the product and its recycle. An important solution for this problem is the application of two-phase systems comprising an aqueous phase containing water-soluble organometallic catalysts and a water immiscible phase (U.S. 31812; CHEMTECH 17, 1987, 570; EP 0107006; Aqueous-Phase Organometallic Catalysis B. Cornils, W. A. Herrmann (Eds.),Wiley-VCH, 1998, Weinheim.). In this case, separation of the organometallic catalyst from organic reactants and products is greatly simplified due to the insolubility of the catalyst in water immiscible phase. The publications New. J. Chem, 1997, 21, 529–531, New. J. Chem, 1997, 21, 857–859 and Catal. Lett., 1997, 47, 43–46 revealed the carbonylation of olefins to carboxylic acids using a biphasic catalyst system ($PdCl_2$/TPPTS) under 50 bar CO pressure at 65–100° C. U.S. Pat. No. 5,536,874 and the publication, J. Chem. Tech. Biotechnol, 1997, 70, 83–91, describe the carbonylation of p-IBPE in a two-phase system wherein one phase is an aqueous medium which contains a water soluble palladium complex and an acid promoter. These processes allow easy separation of the catalyst from the product and its recycle, however, the reaction rates (TOF=0.1 to 50 $h^{-1}$) and 2-arylpropionic acid selectivity (59–74%) were very low under relatively mild reaction conditions (90° C., 450 to 900 psig).

Therefore it is important to develop processes which use new and improved catalysts that give good yields of carboxylic acids under mild reaction conditions with easy separation and reuse of the catalyst.

OBJECTS OF THE INVENTION

It is observed that a novel water soluble transition metal complex provides an improved catalyst for the carbonylation of olefins, organic halides and alcohols to corresponding saturated carboxylic acids under biphasic conditions. The use of such a catalyst gives good yields of carboxylic acids under mild reaction conditions with easy separation and reuse of the catalyst.

Accordingly, an object of the present invention is to provide a process for preparation of carboxylic acids by carbonylation of corresponding olefins, organic halides and alcohols using novel water-soluble palladium complex catalysts under biphasic conditions.

It is another object of the invention to develop a process for the preparation of carboxylic acids by the carbonylation of corresponding olefins, organic halides and alcohols which provides improved yield of the product.

It is another object of the invention to develop a process for the preparation of carboxylic acids by the carbonylation of corresponding olefins, organic halides and alcohols which has improved reaction rates and good regioselectivity to 2-aryl propionic acids.

Another object of the invention is to develop a process for the preparation of carboxylic acids by the carbonylation of corresponding olefins, organic halides and alcohols which provides easy separation and recycle of the catalyst.

Another object of the invention is to develop a simple and efficient process for preparation of carboxylic acids by carbonylation of corresponding olefins, organic halides and alcohols.

SUMMARY OF THE INVENTION

Accordingly, the present invention provides a process for the preparation of a carboxylic acid of the general formula III,

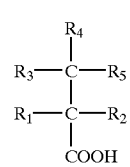

Formula III wherein $R_1$ is aryl, substituted aryl, naphthyl, substituted naphthyl or alkyl, $R_2$, $R_3$, $R_4$ and $R_5$ are independently hydrogen or alkyl, said process comprising reacting the corresponding olefin of formula I or the corresponding organic halide or alcohol of the formula II, Formula I

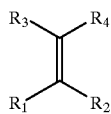

Formula II

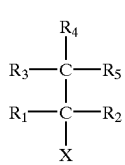

wherein $R_1$ is selected from the group consisting of aryl, substituted aryl, naphthyl, substituted naphthyl or alkyl, $R_2$, $R_3$, $R_4$ and $R_5$ are independently hydrogen or alkyl and X is a halogen atom or a —OH group, in the presence or absence of an organic solvent, a protonic acid, and/or an alkali metal halide, using a novel water soluble palladium complex catalyst of general formula IV Formula IV

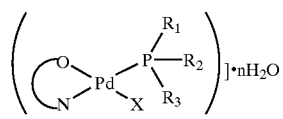

wherein $R_1$, $R_2$ and $R_3$ are substituent on the phosphine ligand and selected from the group consisting of alkyl, aryl, arylalkyl, an cycloaliphatic, at least one of which carries a sulfonic acid and salts thereof, X is aryl or alkyl sulfonato or aryl or alkyl carboxylate or formato or a halide,

is an anionic chelating ligand containing a N donor and O— group, in degassed water with or without excess sulfonated phosphine, in carbon monoxide atmosphere under biphasic conditions, at a temperature ranging between 30 to 130° C., for a period ranging between 0.3 to 24 hrs, at pressures ranging between 50 to 1500 psig, cooling the reaction mixture to ambient temperature, flushing the reaction vessel with inert gas, separating the aqueous catalyst phase and removing the organic solvent, and isolating the compound of formula III from the organic layer.

In one embodiment of the invention, the anionic chelating ligand is selected from the group consisting of 8-hydroxyquinoline, 2-hydroxypyridine, (2-hydroxyethyl)pyridine, pyridil-2-, pyrezyl-2, piperidyl-2-, piperzyl-2-, quinolyl-2-, isoquinolyl-1- and isoquinolyl-2-carboxylates, particularly pyridyl-2-carboxylate, piperidyl-2-carboxylate and 8-hydroxyquinoline.

In another embodiment the sulfonated phosphorous ligand used is a sulfonated mono phosphine.

In a further embodiment of the invention, the sulfonated mono phosphine is selected from the group consisting of tris(sodium-3-sulfonatophenyl)phosphine (TPPTS), phenylbis (sodium-3-sulfonatophenyl) phosphine (TPPDS), diphenyl(sodium-3-sulfonatophenyl) phosphine (TPPMS), methylbis(3-sulfonatophenyl)phosphine, cyclohexylbis (sodium-3-sulfonatophenyl)phosphine, isopropylbis (sodium-3-sulfonatophenyl) phosphine, dimethyl (sodium-3-sulfonatophenyl) phosphine, and dicyclohexyl(3-sulfonatophenyl)phosphine.

In another embodiment the amount of sulfonated phosphine ligand used per gram mole of palladium may be 1–10 mole, preferably 2–3 moles.

In yet another embodiment the halide source if used for the carbonylation reaction may be any of the halide salts such lithium chloride, sodium chloride, potassium chloride, lithium iodide, lithium bromide, sodium bromide, sodium iodide, potassium bromide, potassium iodide, tetrabutyl ammonium chloride, tetrabutyl ammonium bromide and tetrabutyl ammonium iodide or hydro halic acids such as hydrochloric acid, hydrobromic acid and hydroiodic acid.

In another embodiment the protonic acid used may be any of the hydro halic acids such as hydrochloric acid, hydrobromic acid and hydro iodic acid or other protonic acids such as paratoluenesulfonic acid, methanesulfonic acid, triflouromethanesulfonic acid, formic acid, oxalic acid, acetic acid and trifluoroacetic acid.

In yet another embodiment the organic solvent for the carbonylation reaction if used may be benzene, toluene, xylenes, petroleum ether, hexane, heptane, decane, methyl ethyl ketone, chloroform, dichloromethane or diethyl ether.

In another embodiment the concentration of catalyst may be one mole of catalyst for every 50 to 50000 moles of substrate preferably 1 mole of catalyst for every 100 to 10000 moles of substrate and more preferably one mole of catalyst for every 150 to 5000 moles of substrate.

In still another embodiment the amount of halide source per gram mole of catalyst may be in the range of 5 to 500 moles preferably 20 to 300 moles, and more preferably 50 to 200 moles.

In another embodiment the amount of acid source per gram mole of catalyst may be in the range of 5 to 500 moles, preferably 20 to 300 moles, and more preferably 50 to 150 moles.

In a feature of the invention, the reaction can be conveniently carried out in a stirred reactor with the improved catalyst employed with a suitable solvent in presence of carbon monoxide.

The improved process of the present invention is described herein below with examples, which are illustrative only and should not be construed to limit the scope of the present invention in any manner.

EXAMPLE 1

Preparation of the Water-soluble Pd Complex Catalyst IVa 0.0629 mmol of the palladium complex of formula Va {V in which $R'_1$, $R'_2$, $R'_3$=phenyl, X=p-toluenesulfonato (TsO⁻),

=pyridyl-2-carboxylate (prepared as the procedure given in the U.S. Pat. No. 6,069,253)} was dissolved in methyl ethyl ketone (MEK) (10 ml) and shaken vigorously with 2 or 3 equivalents of TPPTS {tris(m-sulfophenyl)phosphine trisodium salt} in degassed water (6 ml). The yellow colour of the MEK layer disappeared and the aqueous layer became yellow in colour indicating the formation of complex IVa in water. For carbonylation reactions, the aqueous layer was used after washing with pure MEK a few times (traces of MEK remains in the aqueous layer). IVa was precipitated from water by adding methanol. The yellow fine suspension of IVa was filtered under argon, washed with methanol and dried under vacuum to yield a yellow fine powder. Anal. Calcd. for $C_{31}H_{23}N\ Na_3O_4PPdS_4 \cdot 6H_2O$: C, 34.598; H, 3.278; N, 1.301; S, 11.916; P, 2.878; Found: C, 34.05; H, 3.28; N, 1.33; S, 12.32; P, 2.50 IR (KBr) 1636 s ($v_{C=O}$), 1397s ($v_{O=O}$), 524s ($v_{Pd-N}$). $^{31}$P ($D_2O$, ppm) $\delta$35.31s (N trans to P), $\delta$36.13w (N cis to P). $^1$H ($D_2O$, ppm) $\delta$2.25 s (3H, tolyl $CH_3$), $\delta$7.2–8 m (Ph and pyridil).

EXAMPLE 2
Hydrocarboxylation of Styrene

A 50 ml stirred autoclave was charged with the following reactants

Styrene: 28.8 mmol

Catalyst having formula IVa prepared as per the procedure described in EXAMPLE 1: 0.0629 mmol in 6 ml degassed water TPPTS:Pd ratio: 2

TsOH: 11.2 mmol

LiCl: 11.2 mmol

Toluene: 15.5 ml

The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 302 $h^{-1}$ and 94.5% conversion of styrene with the formation of a mixture of 2 -and 3-phenylpropionic acids with selectivity of 92 and 7.2% respectively and n/iso ratio of 0.078. The carbonylation products were isolated by evaporation of the solvent followed by acid-base extraction.

EXAMPLE 3
Hydrocarboxylation of Styrene

A 50 ml stirred autoclave was charged with the following reactants

Styrene: 28.8 mmol

Catalyst having formula IVa prepared as per the procedure described in EXAMPLE 1: 0.0629 mmol in 6 ml degassed water TPPTS:Pd ratio: 3

TsOH: 11.2 mmol

LiCl: 11.2 mmol

Toluene: 15.5 ml

The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled and an aliquot of the organic phase sample was withdrawn and analysed by GC. The GC analysis showed TOF of 282 $h^{-1}$ and 93% conversion of styrene with the formation of a mixture of 2- and 3-phenylpropionic acids with selectivity of 90.7% and 8.7 respectively and n/iso ratio of 0.0959.

EXAMPLE 4
Recycle 1

To the final reaction mixture of example 3 under CO, 28.8 mmol of fresh styrene was added. The contents of the autoclave were flushed then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled and an aliquot of the organic phase sample was withdrawn and analysed by GC. The GC analysis showed TOF of 269 $h^{-1}$ and 90% conversion of styrene with the formation of a mixture of 2 -and 3-phenylpropionic acids with selectivity of 91% and 8.6% respectively and n/iso ratio of 0.0945.

EXAMPLE 5
Recycle 2

To the final reaction mixture of example 4 under CO, 28.8 mmol of fresh styrene was added. The contents of the autoclave were flushed then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled and the organic and aqueous layers separated using a separating funnel. The organic layer was analysed by GC. The GC analysis showed TOF of 210 $h^{-1}$ and 80% conversion of styrene with the formation of a mixture of 2 -and 3-phenylpropionic acids with selectivity of.91% and 8.7% respectively and n/iso ratio of 0.095. Pd analysis of the organic layer using atomic absorption spectroscopy showed <0.1 ppm of Pd indicating negligible leaching of Pd. The carbonylation products were isolated by evaporation of the solvent followed by acid-base extraction.

EXAMPLE 6
Hydrocarboxylation of Styrene

A 50 ml stirred autoclave was charged with the following reactants

Styrene: 28.8 mmol

Catalyst having formula IVa prepared as per the procedure described in EXAMPLE 1: 0.0629 mmol in 6 ml degassed water TPPTS:Pd ratio: 2

TsOH: 11.2 mmol

LiCl: 11.2 mmol

Toluene: 15.5 ml

The contents of the autoclave were flushed with nitrogen and then many times with carbon monoxide. Thereafter, the contents were heated to 105° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 124 h$^{-1}$ and 90% conversion of styrene with the formation of a mixture of 2- and 3-phenylpropionic acids with selectivity of 93% and 6.5% and n/iso ratio of 0.07. The carbonylation products were isolated by evaporation of the solvent followed by acid-base extraction.

EXAMPLE 7

Hydrocarboxylation of Styrene

A 50 ml stirred autoclave was charged with the following reactants

Styrene: 28.8 mmol

Aqueous phase separated from EXAMPLE 6: 5.3 ml

Toluene: 15.5 ml

The contents of the autoclave were flushed with nitrogen and then many times with carbon monoxide. Thereafter, the contents were heated to 105° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 100 h$^{-1}$ and 85% conversion of styrene with the formation of a mixture of 2- and 3-phenylpropionic acids with selectivity of 92% and 7.2% respectively and n/iso ratio of 0.078. The carbonylation products were isolated by evaporation of the solvent followed by acid-base extraction.

EXAMPLE 8

Hydrocarboxylation of Styrene

A 50 ml stirred autoclave was charged with the following reactants

Styrene: 57.7 mmol

Catalyst having formula IVa prepared as per the procedure described in EXAMPLE 1: 0.0629 mmol in 6 ml degassed water TPPTS:Pd ratio: 3

TsOH: 11.2 mmol

LiCl: 11.2 mmol

Toluene: 12.5 ml

The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 550 h$^{-1}$ and 91% conversion of styrene with the formation of a mixture of 2- and 3-phenylpropionic acids with selectivity of 95% and 4% respectively and n/iso ratio of 0.0421. The carbonylation products were isolated by evaporation of the solvent followed by acid-base extraction.

EXAMPLE 9

Hydrocarboxylation of 4-isobutyl Styrene

A 50 ml stirred autoclave was charged with the following reactants 4-isobutyl styrene: 57.7 mmol Catalyst having formula IVa prepared as per the procedure described in EXAMPLE 1: 0.0629 mmol in 6 ml degassed water TPPTS:Pd ratio: 3

TsOH: 11.2 mmol

LiCl: 11.2 mmol

Toluene: 15.5 ml

The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 147 h$^{-1}$ and 81% conversion of 4-isobutylstyrene with Ibuprofen [2-(4-isobutylphenyl)propionic acid] selectivity of 98% and 3-(4-isobutylphenyl)propionic acid selectivity of 1.5% and n/iso ratio of 0.0153. The carbonylation products were isolated by evaporation of the solvent followed by acid-base extraction.

EXAMPLE 10

Hydrocarboxylation of 4-tert-butyl styrene

A 50 ml stirred autoclave was charged with the following reactants 4-tert-butyl styrene: 57.7 mmol Catalyst having formula IVa prepared as per the procedure described in EXAMPLE 1: 0.0629 mmol in 6 ml degassed water TPPTS:Pd ratio: 3

TsOH: 11.2 mmol

LiCl: 11.2 mmol

Toluene: 15.5 ml

The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 273 h$^{-1}$ and 81% conversion of 4-tert-butylstyrene with the formation of a mixture of 2- and 3-(4-tert-butylphenyl) propionic acids with selectivity of 96.6 % and 2.8% respectively and n/iso ratio of 0.02898. The carbonylation products were isolated by evaporation of the solvent followed by acid-base extraction.

EXAMPLE 11
Hydrocarboxylation of 6-methoxy-2-vinylnaphthalene

A 50 ml stirred autoclave was charged with the following reactants
- 6-methoxy-2-vinylnaphthalene: 16.67 mmol
- Catalyst having formula IVa prepared as per the procedure described in EXAMPLE 1: 0.0629 mmol in 6 ml degassed water
- TPPTS:Pd ratio: 3
- TsOH: 11.2 mmol
- LiCl: 11.2 mmol
- Toluene: 15.5 ml The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled and the organic and aqueous layers separated using a separating funnel. The organic layer was analysed by GC. The GC analysis showed TOF of 10 h$^{-1}$ and 45.5% conversion of 6-methoxy-2-vinylnaphthalene with Naproxen selectivity of 93% and 3-(6-methoxy-2-naphthyl) propionic acid selectivity of 6.5 % with n/iso ratio of 0.06989. The carbonylation products were isolated by evaporation of the solvent followed by acid-base extraction.

EXAMPLE 12
Hydrocarboxylation of 1-hexene

A 50 ml stirred autoclave was charged with the following reactants
- 1-hexene: 28.8 mmol
- Catalyst having formula IVa prepared as per the procedure described in EXAMPLE 1: 0.0629 mmol in 6 ml degassed water
- TPPTS:Pd ratio: 3
- TsOH: 11.2 mmol
- LiCl: 11.2 mmol
- Toluene: 15.5 ml The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbon monoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 15 h$^{-1}$ and 20% conversion of 1-hexene with the formation of 2-methylhexanoic and heptanoic acids selectivities % and 30% respectively with an n/iso ratio of 0.4615. The carbonylation products were isolated by evaporation of the solvent followed by acid-base extraction.

EXAMPLE 13
Carbonylation of 1-(4-isobutylpheny)ethanol (IBPE)

A 50 ml stirred autoclave was charged with the following reactants
- IBPE: 28.8 mmol
- Catalyst having formula IVa prepared as per the procedure described in EXAMPLE 1: 0.0629 mmol in 6 ml degassed water
- TPPTS:Pd ratio: 3
- TsOH: 11.2 mmol
- LiCl: 11.2 mmol
- Toluene: 15.5 ml The contents of the autoclave were flushed with nitrogen and then many times with carbon monoxide. Thereafter, the contents were heated to 115° C. After the temperature is attained, the autoclave was pressurised to 54 bar with carbonmonoxide, stirring started and it was observed that gas absorption commenced immediately. The pressure in the autoclave was maintained constant using carbonmonoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 18 h$^{-1}$ and 20%. conversion of IBPE with the formation of Ibuprofen and 3-(4-isobutylphenyl)propionic acid selectivities of 98% and 2% respectively with n/iso ratio of 0.0204. The carbonylation products were isolated by evaporation of the solvent followed by acid-base extraction.

EXAMPLE 14
Carbonylation of 1-(4-isobutylphenyl)ethyl chloride (IBPCl)

A 50 ml stirred autoclave was charged with the following reactants
- IBPCl: 5.1 mmol
- Catalyst having formula IVa prepared as per the procedure described in EXAMPLE 1 0.0629 mmol in 6 ml degassed water
- TPPTS:Pd ratio: 3
- TsOH: 11.2 mmol
- LiCl: 11.2 mmol
- Toluene: 17.5 ml The contents of the autoclave were flushed with nitrogen and then many times with carbon monoxide. Thereafter, the contents were heated to 115° C. After the temperature is attained, the autoclave was pressurised to 54 bar with carbonmonoxide, stirring started and it was observed that gas absorption commenced immediately. The pressure in the autoclave was maintained constant using carbonmonoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 5 h$^{-1}$ and 30% conversion of IBPCl with Ibuprofen and 3-(4-isobutylphenyl)propionic acid selectivities of 98% and 2% respectively with n/iso ratio of 0.0204. The carbonylation products were isolated by evaporation of the solvent followed by acid-base extraction.

EXAMPLE 15
Carbonylation of 1-phenylethyl chloride

A 50 ml stirred autoclave was charged with the following reactants
- 1-phenylethylchloride: 5.1 mmol
- Catalyst having formula IVa prepared as per the procedure described in EXAMPLE 1: 0.0629 mmol in 6 ml degassed water TPPTS:Pd ratio: 3
TsOH: 11.2 mmol
LiCl: 11.2 mmol
Toluene: 15.5 ml The contents of the autoclave were flushed with nitrogen and then many times with carbon monoxide. Thereafter, the contents were heated to 115° C. After the temperature is attained, the autoclave was pressurised to 54 bar with carbonmonoxide, stirring started and it was observed that gas absorption commenced immediately. The pressure in the autoclave was maintained constant using carbonmonoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 50 $h^{-1}$ and 45% conversion of 1-phenylethylchloride with 2-phenylpropionic and 3-phenylpropionic acid selectivities of 92% and 6% respectively with n/iso ratio of 0.076. The carbonylation products were isolated by evaporation of the solvent followed by acid-base extraction.

EXAMPLE 16
Hydrocarboxylation of Styrene

A 50 ml stirred autoclave was charged with the following reactants

Styrene: 28.8 mmol
Catalyst having formula IVa prepared as per the procedure described in EXAMPLE 1: 0.0629 mmol in 6 ml degassed water
TPPTS:Pd ratio: 3
HCl: 11.2 mmol
Toluene: 15.5 ml The contents of the autoclave were flushed with nitrogen and then many times with carbon monoxide. Thereafter, the contents were heated to 115° C. After the temperature is attained, the autoclave was pressurised to 54 bar with carbon monoxide, stirring started and it was observed that gas absorption commenced immediately. The pressure in the autoclave was maintained constant using carbonmonoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 139 $h^{-1}$ and 76.5% conversion of styrene with the formation of a mixture of 2- and 3-phenylpropionic acids with selectivity of 76.5% and 23% respectively and n/iso ratio of 0.3006. The carbonylation products were isolated by evaporation of the solvent followed by acid-base extraction.

EXAMPLE 17
Hydrocarboxylation of Styrene

A 50 ml stirred autoclave was charged with the following reactants

Styrene: 28.8 mmol
Catalyst having formula IVa prepared as per the procedure described in EXAMPLE 1: 0.0629 mmol in 6 ml degassed water
TPPTS:Pd ratio: 3
TsOH: 11.2 mmol
LiCl: 11.2 mmol
Cyclohexane: 15.5 ml The contents of the autoclave were flushed with nitrogen and then many times with carbon monoxide. Thereafter, the contents were heated to 115° C. After the temperature is attained, the autoclave was pressurised to 54 bar with carbonmonoxide, stirring started and it was observed that gas absorption commenced immediately. The pressure in the autoclave was maintained constant using carbonmonoxide and the progress of the reaction was monitored by observing the pressure drop and by liquid sampling. The reaction was continued until the pressure drop was too low. The reactor was then cooled, depressurised and the organic and aqueous layers separated using a separating funnel. The organic layer was analysed by GC. The GC analysis showed TOF of 106 $h^{-1}$ and 70% conversion of styrene with the formation of a mixture of 2- and 3-phenylpropionic acids with selectivity of 92% and 8% respectively with n/iso ratio of 0.0869. The carbonylation products were isolated by evaporation of the solvent followed by acid-base extraction.

ADVANTAGES OF THE INVENTION

1. An improved process for carbonylation of olefins, alcohols and organic halides in a biphasic medium under mild reaction conditions.
2. Provides high reaction rates and high regioselectivity to 2-aryl propionic acids.
3. Provides simple and efficient catalyst separation and recycle.

We claim:
1. A process for the preparation of a carboxylic acid of the formula III,

Formula III wherein $R_1$ is aryl, substituted aryl, naphthyl, substituted naphthyl or alkyl, $R_2$, $R_3$, $R_4$ and $R_5$ are independently hydrogen or alkyl, said process comprising the steps of:

a) reacting formula I or formula II,

Formula I

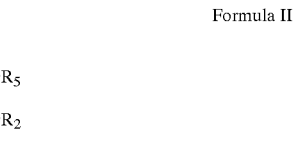

Formula II wherein $R_1$, $R_2$, $R_3$, $R_4$ and $R_5$ are as defined above and X is a halogen atom or a —OH group, in the presence of a protonic acid, and/or an alkali metal halide, with a water soluble palladium complex catalyst of formula IV

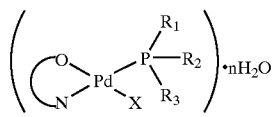

Formula IV wherein $R_6$, $R_7$ and $R_8$ are substituents on the phosphine ligand and selected from the group consisting of alkyl, aryl, arylalkyl, and cycloaliphatic, wherein at least one of $R_6$, $R_7$ and $R_8$ carries a sulfonic acid or sit thereof; Y is aryl, alkyl sulfonato, aryl, alkyl carboxylate, formato or a halide;

is an anionic chelating ligand containing a N donor and O— group, degassed water with or without excess sulfonated phosphine, in a carbon monoxide atmosphere under biphasic conditions, at a temperature ranging between 30 to 130° C., for a period ranging between 0.3 to 24 hrs, at pressures ranging between 50 to 1500 psig;

b) flushing the reaction vessel with inert gas at an ambient temperature;

c) separating the aqueous catalyst phase and removing the organic solvent; and d) isolating the compound of formula III from the organic layer.

2. A process as claimed in claim 1 wherein the reaction of step a) is in the presence of an organic solvent.

3. A process as claimed in claim 1 wherein the anionic chelating ligand is selected from the group consisting of 8-hydroxyquinoline, 2-hydroxypyridine, (2-hydroxyethyl) pyridine, pyridil-2-, pyrezyl-2, piperidyl-2-, piperzyl-2-, quinolyl-2-, isoquinolyl-1- and isoquinolyl-2- carboxylates, particularly pyridyl-2-carboxylate, piperidyl-2-carboxylate and 8-hydroxyquinoline.

4. A process as claimed in claim 1 wherein the sulfonated phosphorous ligand used is a sulfonated mono phosphine.

5. A process as claimed in claim 1 wherein the sulfonated mono phosphine is selected from the group consisting of tris(sodium-3-sulfonatophenyl)phosphine (TPPTS), phenylbis(sodium-3-sulfonatophenyl)phosphine (TPPDS), diphenyl(sodium-3-sulfonatophenyl)phosphine (TPPMS), methylbis(3-sulfonatophenyl)phosphine, cyclohexylbis(sodium-3-sulfonatophenyl)phosphine, isopropylbis(sodium-3-sulfonatophenyl)phosphine, dimethyl(sodium-3-sulfonatophenyl)phosphine, and dicyclohexyl(3-sulfonatophenyl)phosphine.

6. A process as claimed in claim 1 wherein the amount of sulfonated phosphine ligand used per gram mole of palladium is 1–10 moles.

7. A process as claimed in claim 6 wherein the amount of sulfonated phophine ligand used per gram of the mole of palladium is 2–3 moles.

8. A process as claimed in claim 1 wherein the halide source if used for the carbonylation reaction is a halide salt selected from the group consisting of lithium chloride, sodium chloride, potassium, chloride, lithium iodide, lithium bromide, sodium bromide, sodium iodide, potassium bromide, potassium iodide, tetrabutyl ammonium chloride, tetrabutyl ammonium bromide and tetrabutyl ammonium iodide or a hydro halic acid selected from the group consisting of hydrochloric acid, hydrobromic acid and hydroiodic acid.

9. A process as claimed in claim 1 wherein the protonic acid used is a hydro halic acid selected from the group consisting of hydrochloric acid, hydrobromic acid and hydro iodic acid or a protonic acid selected from the group consisting of paratoluenesulfonic acid, methanesulfonic acid, triflouromethanesulfonic acid, formic acid, oxalic acid, acetic acid and trifluoroacetic acid.

10. A process as claimed in claim 2 wherein the organic solvent for the carbonylation reaction if used is selected from the group consisting of benzene, toluene, xylenes, petroleum ether, hexane, heptane, decane, methyl ethyl ketone, chloroform, dichloromethane and diethyl ether.

11. A process as claimed in claim 1 wherein the concentration of catalyst is one mole of catalyst for every 50 to 50000 moles substrate.

12. A process as claimed in claim 11 wherein the concentration of catalyst is 1 mole of catalyst for every 100 to 10000 moles of substrate.

13. A process as claimed in claim 11 wherein the concentration of catalyst is one mole of catalyst for every 150 to 5000 moles of substrate.

14. A process as claimed in claim 1 wherein the amount of halide source per gram mole of catalyst is in the range of 5 to 500 moles.

15. A process as claimed in claim 14 wherein the amount of halide source per gram mole of catalyst is in the range of 20 to 300 moles.

16. A process as claimed in claim 15 wherein the amount of halide. source per gram mole of catalyst is in the range of 50 to 200 moles.

17. A process as claimed in claim 1 wherein the amount of acid source per gram mole of catalyst is in the range of 5 to 500 moles.

18. A process as claimed in claim 17 wherein the amount of acid source per gram mole of catalyst is in the range of 20 to 300 moles.

19. A process as claimed in claim 18 wherein the amount of acid source per gram mole of catalyst is in the range of 50 to 150 moles.

20. A process as claimed in claim 1 wherein the reaction is carried out in a stirred reactor with the catalyst of formula IV used with a suitable solvent in presence of carbon monoxide.

* * * * *